United States Patent
Proto

[19]

[11] Patent Number: 6,056,771
[45] Date of Patent: *May 2, 2000

[54] RADIUSED TIP SURGICAL NEEDLES AND SURGICAL INCISION MEMBERS

[75] Inventor: George R. Proto, West Haven, Conn.

[73] Assignee: United States Surgical Corporation, Norwalk, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/835,783

[22] Filed: Apr. 15, 1997

Related U.S. Application Data

[63] Continuation of application No. 08/460,356, Jun. 2, 1995, abandoned.

[51] Int. Cl.⁷ .................................................. A61B 17/06
[52] U.S. Cl. ........................... 606/222; 606/223; 606/224
[58] Field of Search ................. 606/222–226, 606/144–145, 147, 148, 139; 223/102–104; 163/2, 5; 604/272; 289/16; 112/222

[56] References Cited

U.S. PATENT DOCUMENTS

| | | | |
|---|---|---|---|
| 1,558,037 | 10/1925 | Morton | 606/224 |
| 2,411,079 | 11/1946 | Baule | 606/226 |
| 2,516,710 | 7/1950 | Mascolo | 606/223 |
| 4,236,470 | 12/1980 | Stenson | 606/145 |
| 4,966,143 | 10/1990 | Meinershagen . | |
| 5,123,910 | 6/1992 | McIntosh . | |
| 5,342,397 | 8/1994 | Guido . | |
| 5,383,901 | 1/1995 | McGregor et al. . | |
| 5,389,103 | 2/1995 | Melzer et al. | 606/144 |
| 5,478,344 | 12/1995 | Stone et al. | 606/144 |
| 5,569,301 | 10/1996 | Granger et al. . | |

FOREIGN PATENT DOCUMENTS

| | | | |
|---|---|---|---|
| 619984 | 10/1994 | European Pat. Off. | 606/223 |

OTHER PUBLICATIONS

Drilled End Surgical Needles, B. G. Sulzle, Inc., Oct. 1986, Reprinted Jul. 1991, 13 pages.

Considerations in the Choice of Surgical Needles, By William C. Trier, M.D., F.A.C.S., The Surgeon's Library, Surgery, Gynecology & Obstetrics, Jul. 1979, vol. 149, pp. 84–94.

Ethiguard Sutures—The pointless needle that makes a lot of sense., Ethicon, 1992, 2 pages.

Surgical Atlas & Suture Selection Guide, Davis & Geck, Medical Device Division, Apr. 4, 1990, Chicago, Ill., 4 pages.

*Primary Examiner*—Michael Buiz
*Assistant Examiner*—Tina T. D. Pham

[57] ABSTRACT

A surgical needle or surgical incision member is provided including a body portion defining first and second longitudinal ends, a radiused tissue penetrating portion adjacent at least one longitudinal end of the body portion having a radius of approximately 0.005 to 0.015 inches, suture attachment structure formed in the body portion and a suture attached to the suture attachment structure. A method of suturing is also provided wherein the surgical needle may be passed through tissue while minimizing trauma to adjacent bony structures or the like.

2 Claims, 7 Drawing Sheets

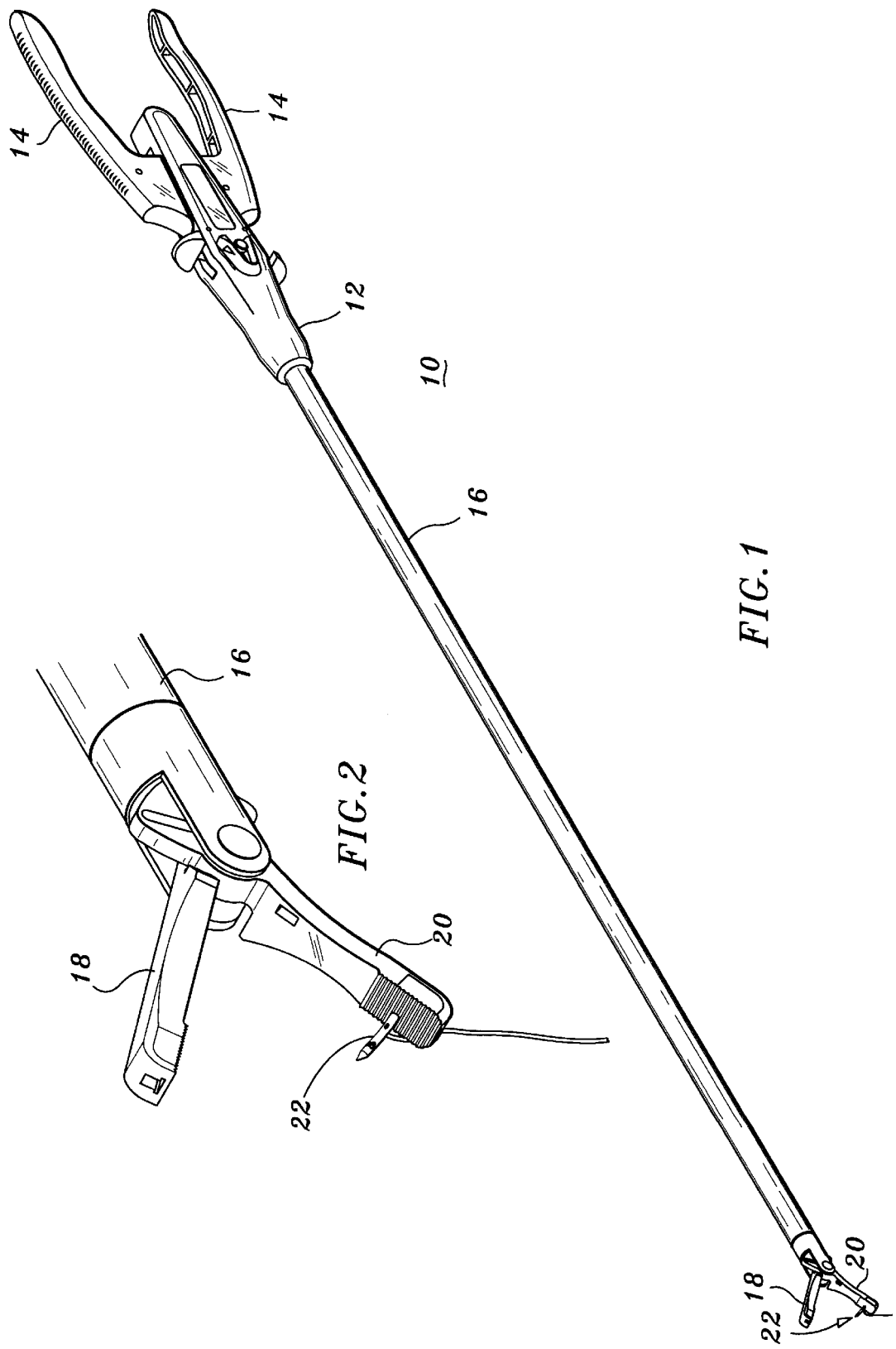

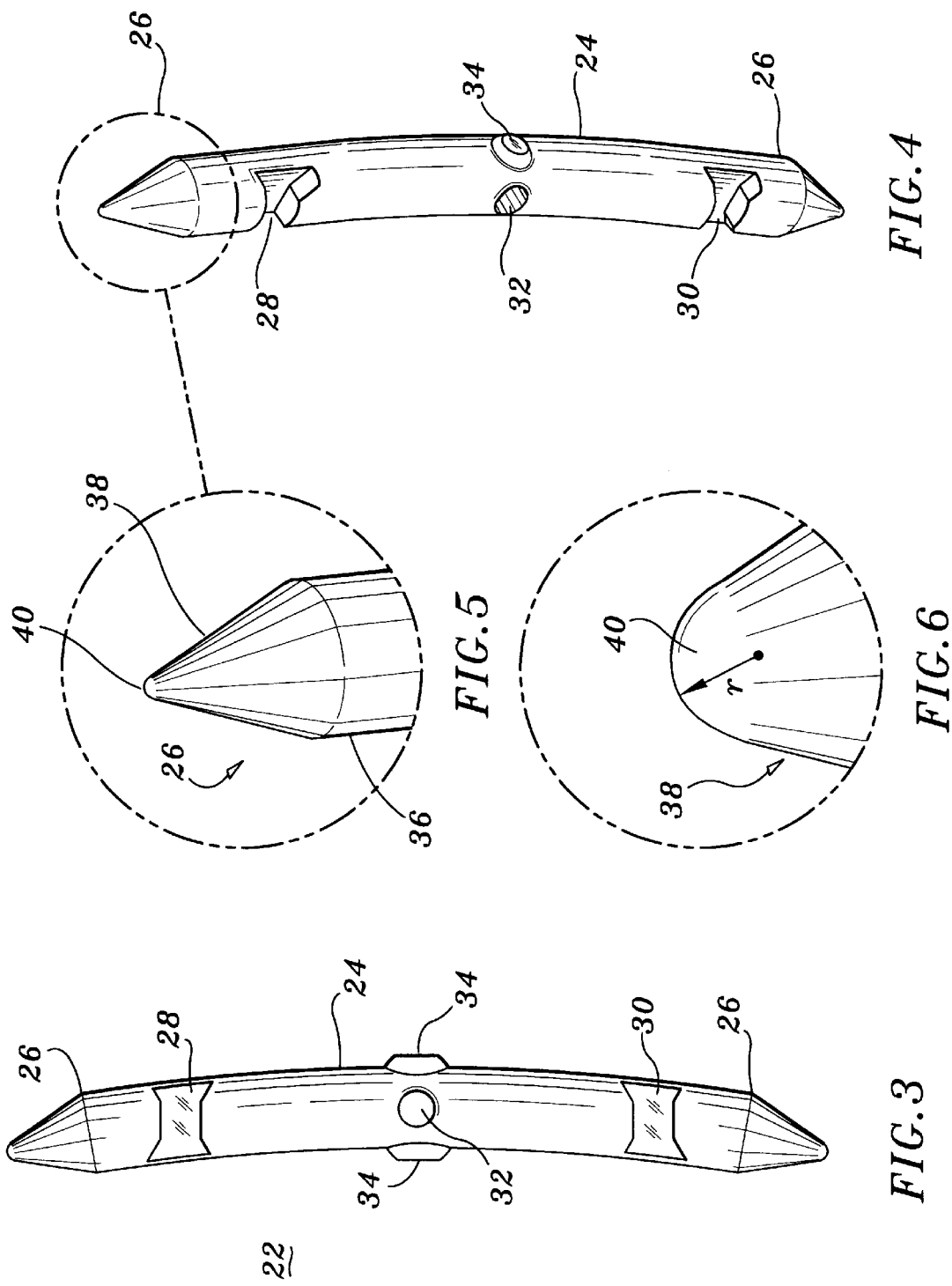

RADIUSED TIP SURGICAL NEEDLES AND SURGICAL INCISION MEMBERS

This is a continuation of U.S. application Ser. No. 08/460,356 filed on Jun. 2, 1995 now abandoned.

BACKGROUND

1. Technical Field

This application relates generally to surgical suturing instrumentation and, more particularly to surgical needles and surgical incision members used in conjunction with endoscopic or laparoscopic suturing apparatus.

2. Description of Related Art

Endoscopic or laparoscopic procedures are characterized by the use of an elongated cannula structure having a relatively small diameter with a proximal and distal end. The distal end is passed through the surrounding tissue into a body cavity wherein the surgical procedure or examination is to be effected, thus providing a conduit for the insertion of surgical instrumentation. A plurality of cannula structures may be used to allow insertion of a variety of instruments simultaneously during a given procedure. For example, one cannula may provide a conduit for an endoscope for vision and illumination within the operative cavity, while other cannulas may provide conduits for control of specialized surgical instruments designed for performing specific procedural functions.

Surgical procedures often require placing stitches through tissue, a procedure traditionally accomplished by hand. In endoscopic and laparoscopic surgical procedures, suturing internal body tissue presents a particularly challenging task. In such minimally invasive type surgical procedures, suturing must be accomplished through a cannula port that typically averages between five and ten millimeters in diameter. As used herein, the term "surgical needle" refers to needles having tissue penetrating portions on a least one longitudinal end, while the term "surgical incision member" refers to a particular type of surgical needle having tissue penetrating portions adjacent both longitudinal ends. Surgical incision members are particularly suited for use with surgical suturing instrumentation.

One instrument for facilitating laparoscopic suturing is described in commonly assigned U.S. patent application Ser. No. 08/134,145, filed Oct. 8, 1993, which is incorporated herein by reference. That instrument effects endoscopic suturing by passing a double pointed surgical incision member back and forth through tissue using a unique jaw structure. This jaw structure allows the surgeon to alternately lock the surgical incision member in the first or second jaw. In this manner, tissue can be sutured simply by opening and closing the jaw structure while alternately engaging opposite ends of the surgical incision member.

The shape and design of the surgical incision member is an important aspect of the operation of endoscopic or laparoscopic suturing apparatus. For example, the incision member should be configured to fit down a cannula, preferably transverse to the cannula axis, and easily penetrate tissue when moved in either longitudinal direction with a minimal incision. The surgical incision member should also be capable of drawing an attached suture through the incision with little or no additional trauma to the incision. Unlike conventional surgical needles wherein the tissue penetrating portion or point is sharp or has cutting edges, when operating on tough tissue around or near bony structures, the tissue penetrating portions of the surgical incision member should be relatively blunt or radiused to avoid or minimize trauma to the bony structures and surrounding tissues.

SUMMARY

A surgical needle is disclosed having a body portion defining first and second longitudinal ends, a relatively blunt or radiused-tip tissue penetrating portion positioned adjacent at least one of the first and second longitudinal ends and suture attachment structure defined therebetween. The relatively blunt or radiused-tip tissue penetrating portion preferably has a substantially spherical radius of approximately 0.005 to 0.015 inches, more preferably 0.005 to 0.010 inches and still more preferably about 0.007 inches. The surgical needle has a penetrating portion at at least one end thereof. Preferably, the body portion of the surgical needle has relatively blunt or radiused-tip penetrating portions adjacent both the first and second longitudinal ends to form a surgical incision member. The body portion of such a surgical incision member is preferably curved and of uniform cross-section and further includes first and second apparatus engagement structures for effecting alternate engagement with the jaws of a surgical suturing apparatus. The first and second engagement structures are preferably recesses formed adjacent the first and second longitudinal ends of the curved body portion of the surgical needle. The suture attachment structure may include a transverse bore configured to facilitate the attachment of a length of suture therein. In the case of a straight or curved surgical needle having a penetrating portion at one end thereof, the suture may be attched at the other end therof. See, for example, U.S. patent application Ser. No. 08/192,936 filed Feb. 7, 1994, which is hereby incorporated by reference.

The surgical incision member may further include compression structure which allows the incision member to be crimped or swaged to anchor the suture into the suture attachment structure. In one embodiment at least one protrusion or bulge is positioned on an outer surface of the curved body portion adjacent the transverse bore. The suture is positioned in the bore and the incision member is compressed or swaged so as to force a volume of material into the bore and into contact with the suture therein. Preferably, the at least one protrusion is configured to conform to at least a portion of the circular body. In this configuration, upon compression of the protrusion, material is displaced into the transverse bore while maintaining a substantial uniform cross-section along the body.

A method is also provided for suturing tissue sections while minimizing trauma to adjacent bony structures. The method includes providing a surgical needle having a body portion, a substantially spherical or blunt tissue penetrating portion on at least one end of the body portion, and a length of suture affixed to the body portion. A first tissue section is penetrated with the surgical needle. In the event that bony structure or the like is encountered, the blunt tissue penetrating portion may be moved or slid along an outer surface of the bony structure with minimal trauma to the tissue structures and without permanent deformation of the needle. A second tissue section is then penetrated with the surgical needle and the surgical needle is drawn through the first and second tissue sections to draw the length of suture through the first and second tissue sections.

BRIEF DESCRIPTION OF THE DRAWINGS

Various embodiments are described hereinbelow with reference to the drawings, wherein:

FIG. 1 is a perspective view of an exemplary surgical suturing apparatus;

FIG. 2 is an enlarged view of the distal end of the apparatus of FIG. 1;

FIG. 3 is a side view of one embodiment of a surgical incision member illustrating radiused-tip tissue penetrating portions at either end, a suture attachment aperture and crimping bulges, and apparatus engagement structure;

FIG. 4 is a perspective view of the surgical incision member of FIG. 3;

FIG. 5 is an enlarged perspective view of a radiused-tip tissue penetrating portion of the embodiment of FIG. 4;

FIG. 6 is a still further enlarged perspective view of radiused-tip tissue penetrating tip portion of FIG. 5 illustrating preferred substantially spherical radii "r";

DETAILED DESCRIPTION OF PREFERRED EMBODIMENTS

Figure 9:
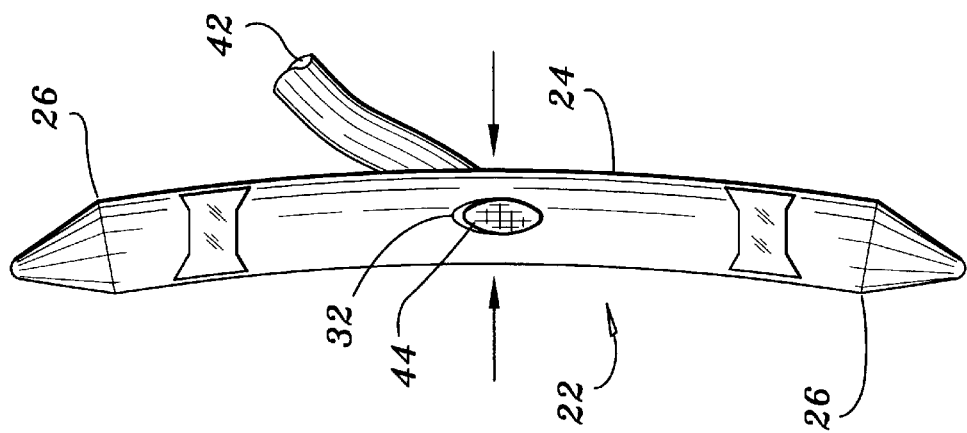
FIG. 9 shows the body portion of FIG. 7 rotated after crimping.

Referring now to the drawings and in particular to FIGS. 1 and 2, there is shown an exemplary embodiment of a suturing apparatus used in conjunction with the various surgical incision member configurations. While the following disclosure is directed particularly to surgical incision members, the innovative features disclosed herein are equally applicable to, and contemplated for use with, all types of surgical needles. The suturing apparatus, generally indicated by reference numeral 10, has a handle housing 12 having a two-armed handle 14, an elongated tubular housing or body portion 16, and two jaws 18 and 20. Handle 14 is used to control the opening and closing of jaws 18 and 20 and is designed to move in the same plane as jaws 18 and 20 to provide an ergonomic advantage. Handle housing 12 may also be rotatably connected to body portion 16 to provide further ergonomic advantage. This embodiment is particularly well adapted for use in endoscopic or laparoscopic procedures as the tubular housing 16 is preferably dimensioned to be deployable into a body cavity through a tubular cannula structure of between about 5 mm to about 10 mm in internal diameter.

Preferred embodiments of surgical incision members which may be utilized with the above-described apparatus will now be described. Referring to FIG. 3, in a preferred embodiment, a surgical incision member 22 includes a body portion 24 and relatively blunt or radiused-tip tissue penetrating portions 26 adjacent each end of the body portion 24. As noted hereinabove, while the following description discloses a surgical incision member, a surgical needle having a single relatively blunt or radiused-tip tissue penetrating portion on an end thereof is also contemplated herein. The body portion 24 of the surgical incision member is preferably arcuate in shape and has a radius of curvature which preferably corresponds to the arc defined by the motion of the jaws 18 and 20. Preferably, the body portion 24 has a substantially uniform circular cross-section. However, alternative cross-sectional embodiments are contemplated. For example, the cross-section of the body portion 24 may be square, rectangular, triangular or hollow-ground. The surgical incision member may be manufactured using known metal injection molding (MIM) techniques. Preferably, the surgical incision member is formed on an apparatus disclosed in U.S. patent application Ser. No. 08/458,213 on even date, herewith and entitled PROGRESSIVE DIE/CARRIER APPARATUS AND METHODS OF FORMING SURGICAL NEEDLES, the disclosure of which is incorporated by reference herein. Alternatively, more traditional types of needle forming techniques may be utilized including extruding, cutting, bending, grinding and polishing wire stock.

In the embodiment shown in FIGS. 3 and 4, the body portion 24 includes apparatus engagement structure shown as recesses 28 and 30 which are configured to alternatively engage securing blades of the suturing apparatus as described in detail hereinbelow. As shown in FIG. 3, recesses 28 and 30 include tapered lead-in portions 28a and 30a which facilitate seating of securing blades within each respective recess. Suture attachment structure, in this embodiment shown as aperture 32, is positioned intermediate the ends 26 of the surgical incision member 22, and is preferably positioned adjacent the approximate center of body portion 24. The aperture 32 is configured to receive a suture and facilitate securement of the suture to surgical incision member 22, as will be described below. Bulges 34 are provided in body portion 24 adjacent aperture 32 to facilitate securement of the suture therein.

Referring now to FIGS. 4–6, surgical incision member 22 is provided with relatively blunt or radiused-tip tissue penetrating portions 26 so as to avoid penetration into bony structure or other relatively hard tissues. By forming the penetrating portions with blunt tips, in the event that bony structures or like hard tissue is encountered by the surgical incision member or surgical needle during suturing, the surgical incision member or needle moves or slides, i.e., is "skived" along such bony structures without danger of scratching the bony structure or penetration therein and with minimal trauma thereto as might be the case with a sharply pointed or cutting tip needle. Radiused-tip tissue penetrating portions 26 generally include a cylindrical portion 36 which preferably has a same diameter as body portion 24 and a conical portion 38. Because the tip does not penetrate the bony or hard tissue, the likelihood of bending the surgical incision member or needle is reduced.

As shown in FIGS. 5 and 6, conical portion 38 is provided with a relatively blunt spherical tip 40 having a spherical radius "r". In the preferred embodiment the preferred spherical radius "r" is on the order of approximately 0.005 to 0.015 inches. Preferably the spherical radius "r" is on the order of 0.005 to 0.010 inches. The optimal radius for the spherical radius "r" is about 0.007 inches which has been found to provide optional tissue penetration, even in tough tissues, such as, for example, Cooper's ligament, while being sufficiently blunt to prevent over penetration into bony structure or other unintended hard tissues. While the disclosed surgical incision members include relatively blunt or spherical tips, forms of substantially blunt tips, other than spherical tips, may be useful.

Figure 8:
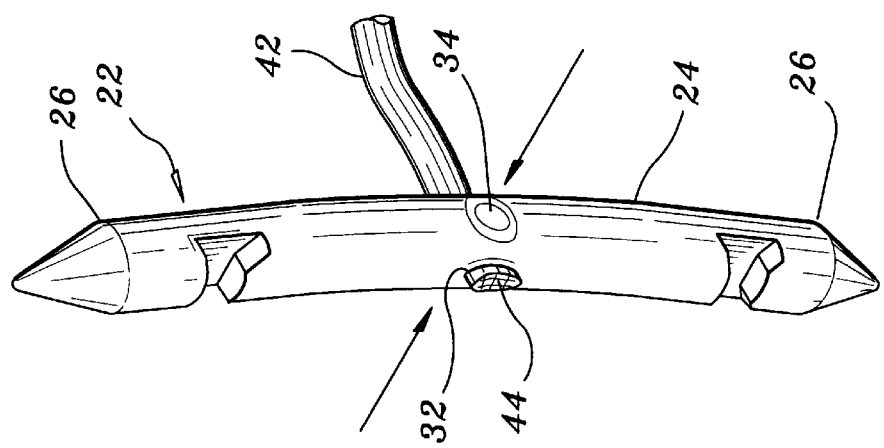
FIG. 8 illustrates the body portion of the surgical incision member of FIG. 7 crimped on the suture.
Figure 7:
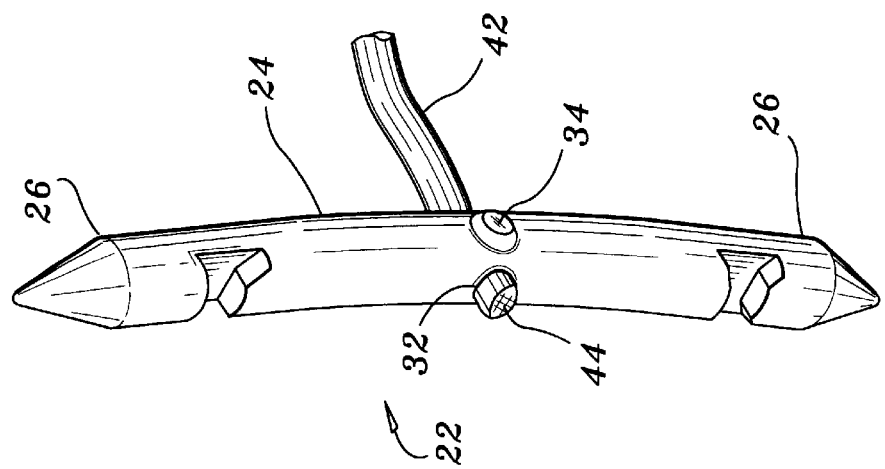
FIG. 7 shows a suture positioned within the body portion of the surgical incision member of FIG. 4 in preparation for crimping the suture to the surgical incision member.

Referring now to FIGS. 7–9, in order to secure a length of suture 42 within aperture 32 in body portion 24, suture 42 is inserted through suture attachment aperture 32 until a tip portion 44 of the suture 42 passes through aperture 32 and suture material occupies the aperture 32. Both monofilament and multifilament sutures are contemplated for use with the surgical incision member disclosed herein. Preferably, where a multifilament suture is to be used, one end thereof is tipped to facilitate insertion of the suture into the suture attachment structure. Where monofilament sutures are to be used, no such tipping is required. Where an adhesive is used, the adhesive is applied from one or both ends of aperture 32 and wicks into the suture so as to surround the suture and fill suture attachment aperture 32. Suitable adhesives include medical grade cyanoacrylate glue, epoxy cements and other medically acceptable adhesives.

Alternatively, as shown in FIGS. 8 and 9, suture 42 may be attached to the surgical incision member 22 by crimping or swaging the body portion 24 adjacent suture attachment aperture 32 with one or more dies so as to compress the bulges 34 and thus body portion into the aperture 32 and crimp the suture into the aperture as disclosed in detail in U.S. patent application Ser. No. 08/260,579. Once the suture is attached, any excess portion of the suture extending through the needle is preferably cut off flush with the surface of the body portion 24 to minimize trauma to tissue. Preferably a pair of dies (not shown) impact bulges 34, to crimp the body portion 24 and attach the suture 42 thereto by compression force. Preferably, each die has a curved surface with a radius of curvature corresponding to the radius of curvature of circular body portion 24. Thus, when the dies impact bulges 34, material of the body portion is compressed toward the center of aperture 32 and the volume of material of each bulge 34 is displaced inwardly to occupy the portion of the body which has been deformed to engage the suture. As a result, a substantially uniform cross-section is maintained throughout the length of the body portion 24, including the suture attachment region. Maintaining the uniform circular cross-section along the length of the surgical incision member minimizes the force required to pass through tissue and also minimizes trauma to the tissue by minimizing the incision size. FIG. 9 illustrates the cross-section of the suture attachment region after the dies have impacted the surgical incision member.

Figure 10:
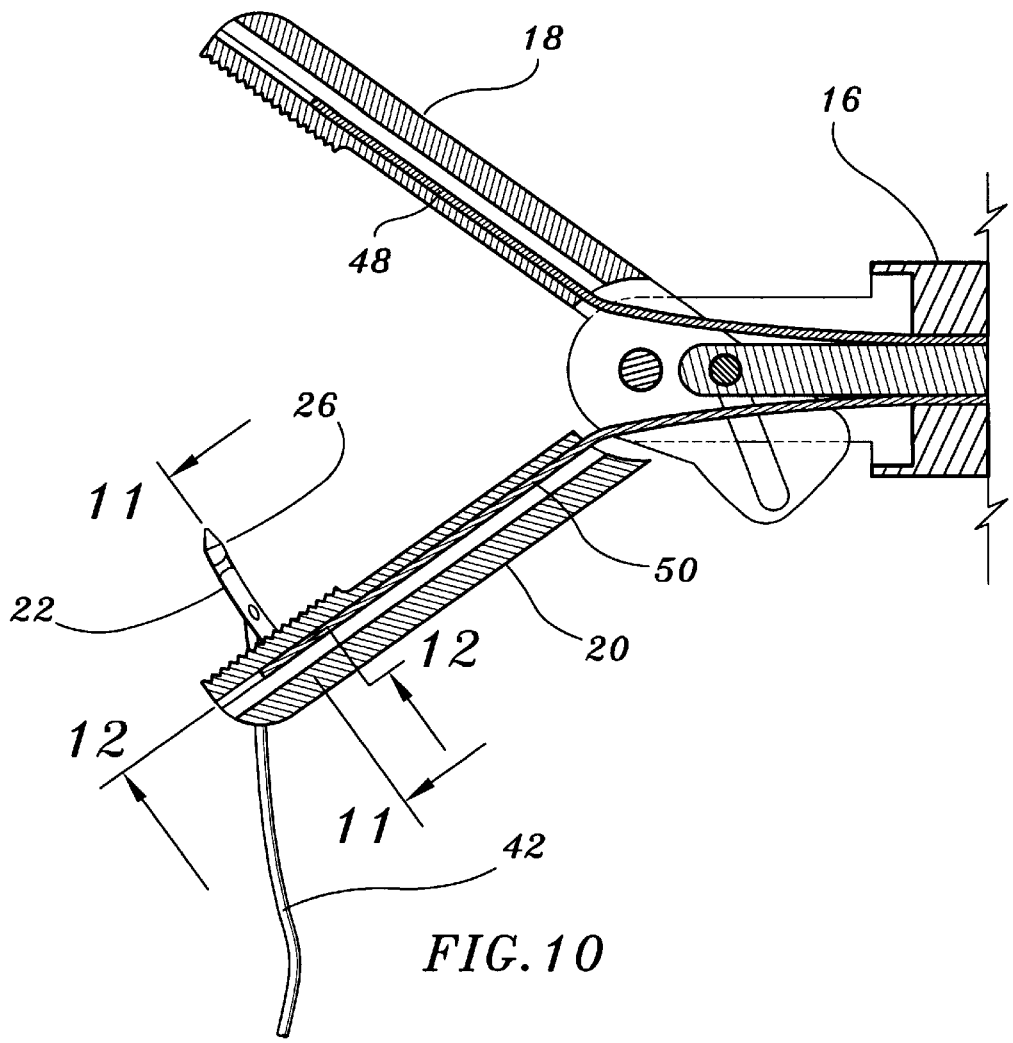
FIG. 10 is a plan view in cross-section of the distal end of the apparatus of FIG. 1, illustrating the jaws in an open position and a surgical incision member secured in the lower jaw.
Figure 11:
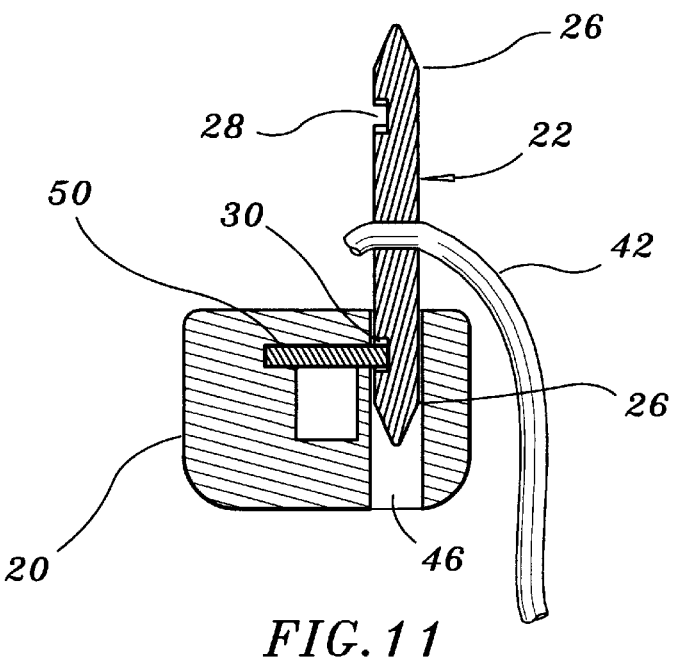
FIG. 11 is a enlarged cross-sectional view taken along the line 11—11 of FIG. 10 and illustrating the blade member securing the surgical incision member within the bottom jaw.
Figure 12:
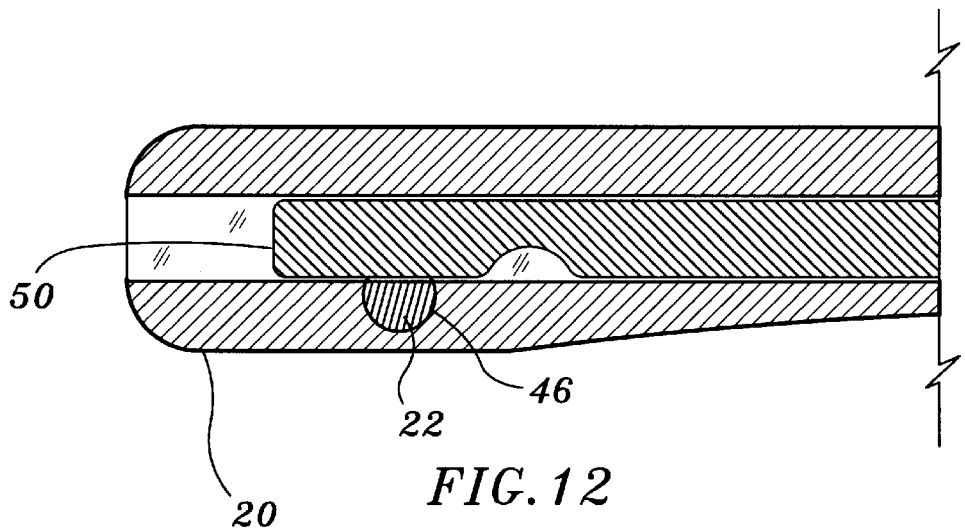
FIG. 12 is a view taken along the line 12—12 of FIG. 10.
Figure 13:
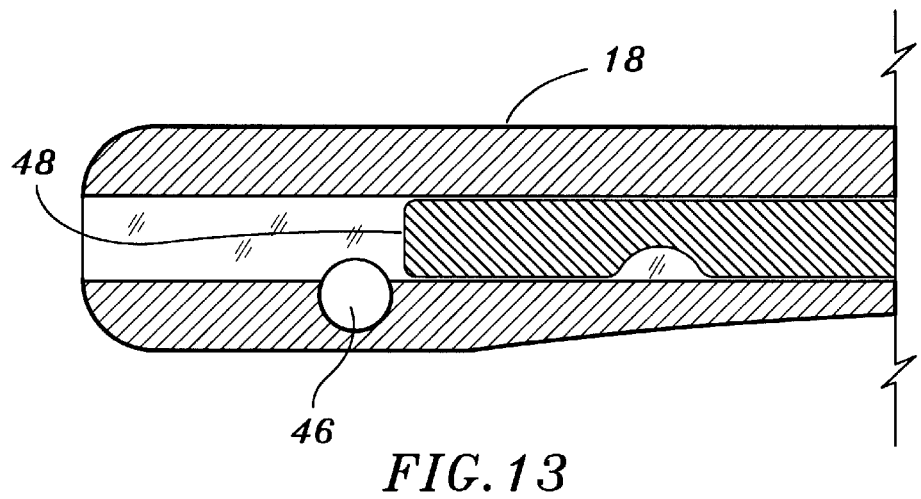
FIG. 13 is a partial cross-sectional view of the upper jaws with a blade member in a disengaged position.

Referring to FIGS. 10 and 11, each jaw of apparatus 10 is adapted to receive a portion of a surgical incision member 22 in recesses 46 (FIG. 11). When jaws 18 and 20 are closed, the surgical incision member 22 sits in the recesses 46 in both jaws. When the jaws are opened, the surgical incision member 22 is retained in one jaw recess 46 depending upon which blade 48 or 50 intersects the surgical incision member 22 through recess 46. As shown in FIGS. 10–13, blade 50, for example, cooperating with lower jaw 20 has been extended through a channel 51 in lower jaw 20 and into recess 46 to secure surgical incision member 22 thereto. Alternatively, blade 48 may extend through a channel 49 in upper jaw 18 and intersect surgical incision member 22 through recess 46, thus securing surgical incision member 22 in upper jaw 18. The movement of the blades to engage the surgical incision member 22 is described in more detail in U.S. application Ser. No. 08/134,145 incorporated by reference hereinabove.

Figure 14:
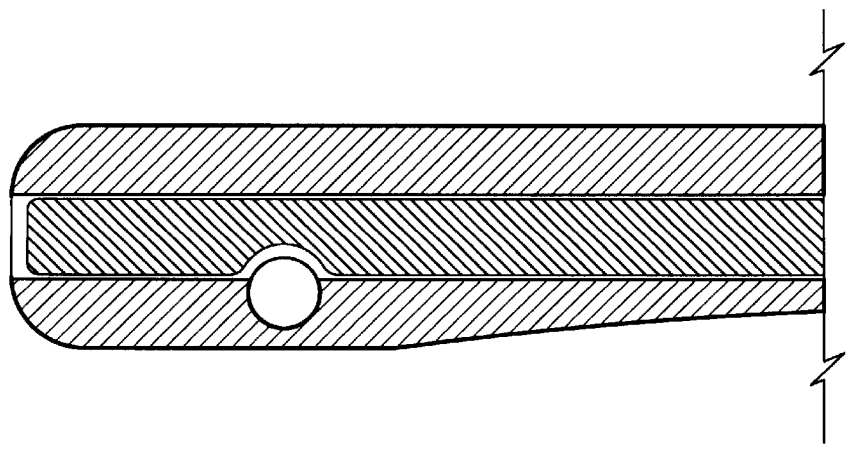
FIG. 14 is a partial cross-sectional view of a jaw with the blade member in a loading position.

FIG. 14 illustrates a loading gap 52 provided in at least one of blades 48 or 50 which, when aligned with recess 46, facilitates loading of surgical incision member 22 within a jaw of apparatus 10.

Figure 15:
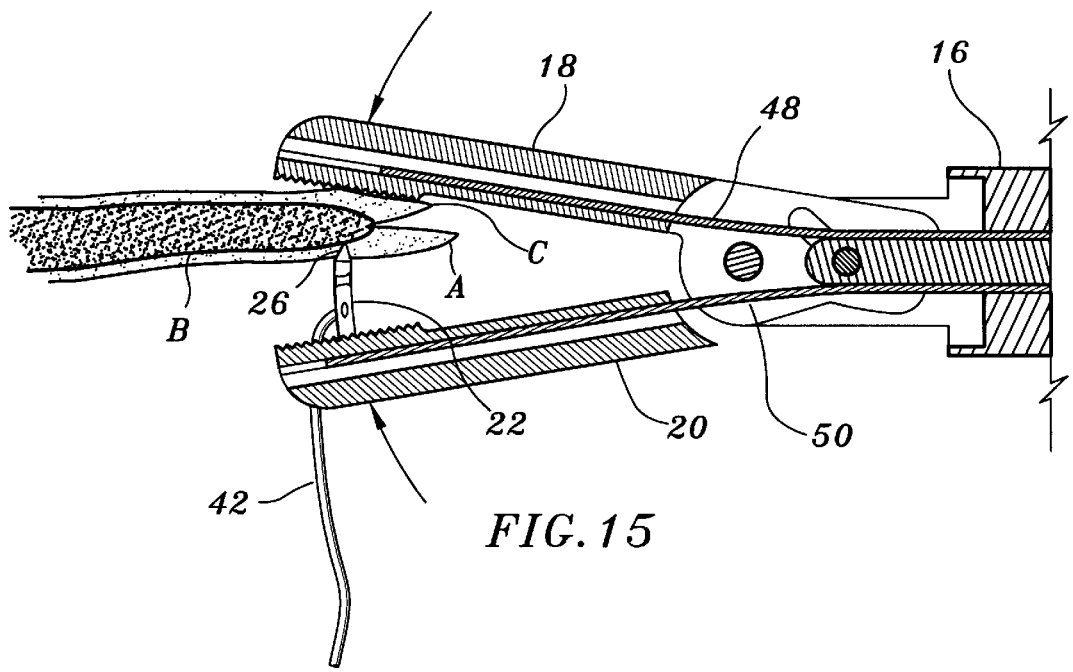
FIG. 15 shows a side view, in partial cross-section, of a suturing apparatus loaded with a surgical incision member adjacent tissue to be sutured, the surgical incision member being passed through the first tissue section by the suturing apparatus and encountering bony structure.
Figure 16:
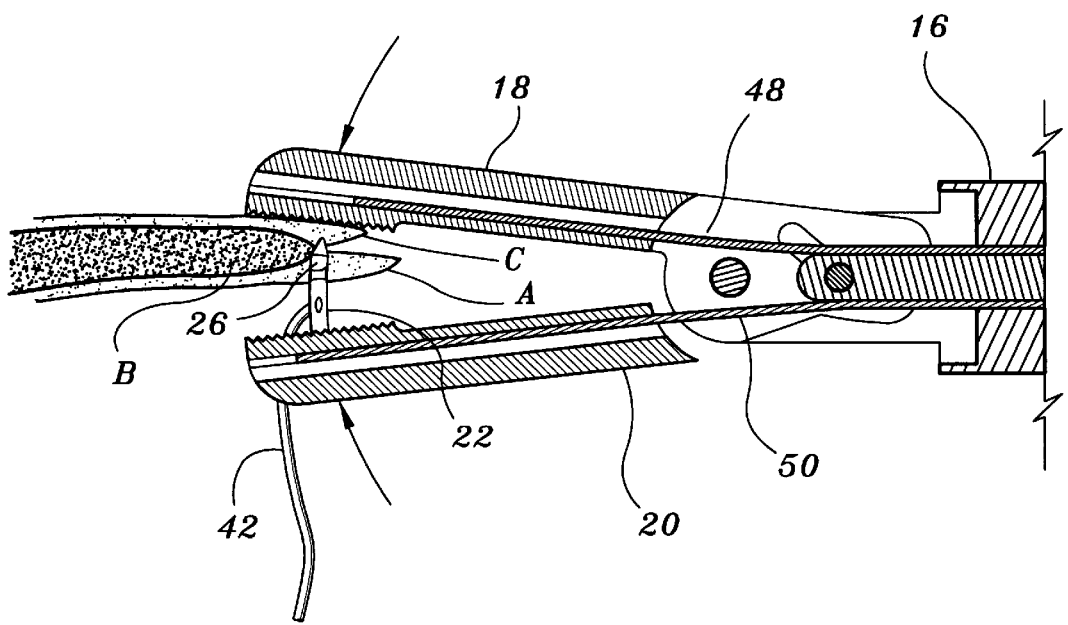
FIG. 16 shows the surgical incision member being forced through the first and second tissue sections by closure of the jaws.
Figure 17:
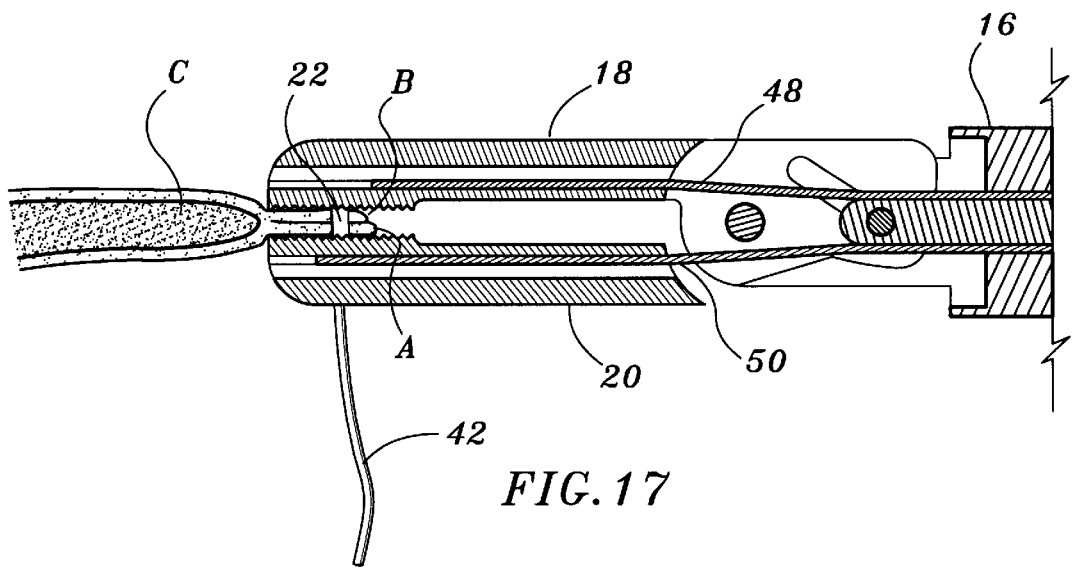
FIG. 17 shows the jaws in a fully closed position after penetrating both the first and second tissue sections.

Referring to FIGS. 15–18, in conjunction with FIGS. 1 and 2, in order to operate the prepared suturing apparatus 10, the open jaws 18 and 20 mounting a surgical incision member 22 are positioned around the tissue to be sutured. As shown in FIG. 15, the surgical incision member 22 is initially secured to lower jaw 20 by blade 50. Handles 14 are approximated toward each other, closing the jaws 18 and 20 around the tissue so that the surgical incision member 22 penetrates a first tissue section A. When suturing in the vicinity of bony structures and the like, for example, bony structure B, it is possible that the tip of the surgical incision member may encounter and contact bony structure B. Should this occur, surgical incision member 22 does not penetrate bony structure B, but rather moves or "skives" along the structure with minimal trauma thereto until surgical incision member 22 is clear of bony structure B. As noted hereinabove, the spherical radius of radiused tip tissue penetrating portion 26 helps prevent penetration of surgical incision member 22 into bony structure B and hence, reduces the likelihood of bending the surgical incision member during use due to contact with bony structures. Because the surgical incision member is contemplated for use in endoscopic procedures, reducing the likelihood of bending the needle due to contact with bony tissue advantageously reduces the incidence of having to remove the suturing instrument from the endoscopic surgical field to replace a damaged surgical incision member.

Figure 18:
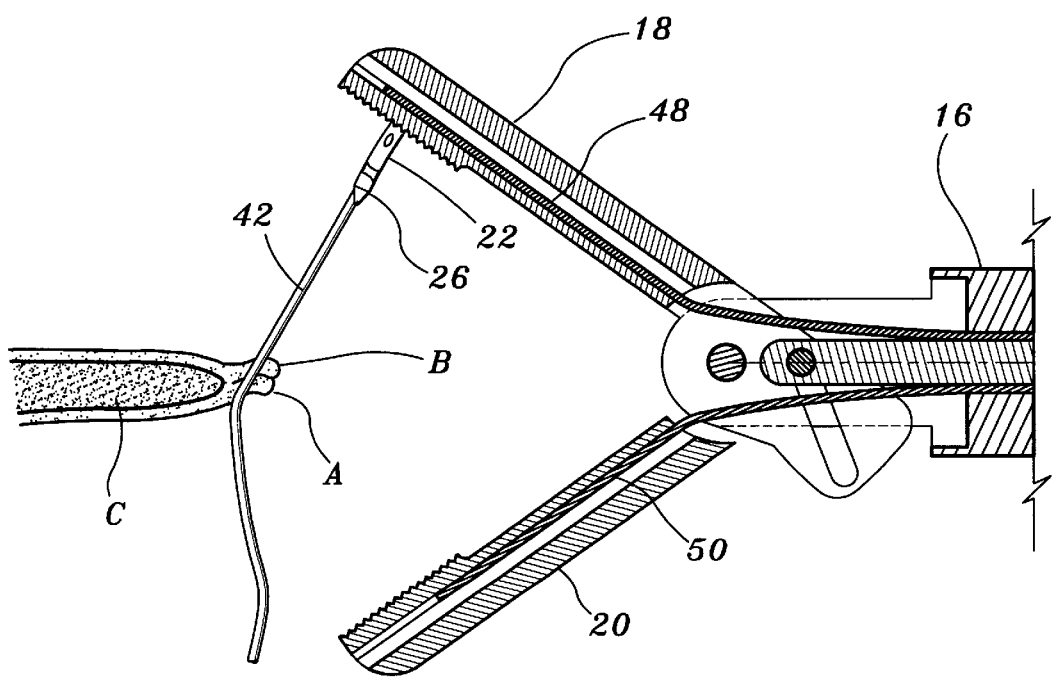
FIG. 18 shows the jaws in an open position and the suture being drawn through the first and second tissue sections.

Once surgical incision member 22 is clear of bony structure B, jaws 18 and 20 may be fully closed about tissue sections A and C. Surgical incision member 22 thus penetrates tissue sections A and C and is guided into recess 46 in jaw 18. The jaws are then opened, as shown in FIG. 18, and the suture 42 is pulled through the tissue sections. The surgical incision member is thereby ready to make another stitch by repeating the above described steps.

It will be understood that various modifications can be made to the embodiments disclosed herein. For example, as noted above, the relatively blunt or radiused-tip is not limited to use only with surgical incision members but may find application in various manner of straight, single bluntly pointed or otherwise configured surgical needles. Various sizes of the surgical incision members are contemplated, as well as surgical incision members having various types of cross-sections. Apertures as used herein are not limited to through bores and include blind holes. Therefore, the above description should not be construed as limiting, but merely as exemplification of preferred embodiments. Those skilled in the art will envision other modifications within the scope and spirit of the claims appended hereto.

What is claimed is:

1. A method of suturing tissue with minimal trauma to bony structure comprising the steps of:

a) providing a surgical needle having a body portion, a relatively blunt tissue penetrating portion on at least one end of the body portion having a radius of approximately 0.005 to 0.015 inches, and a length of suture affixed to the body portion;

b) penetrating a first tissue section with the surgical needle;

c) moving the relatively blunt tissue penetrating portion along the surface of bony structure without penetration thereof;

d) penetrating a second tissue section with the surgical needle; and e) drawing the surgical needle through the first and second tissue sections to draw the length of suture through the first and second tissue sections.

2. A method of endoscopically suturing tissue with minimal trauma to bony structure comprising the steps of:

a) mounting a surgical needle to an endoscopic suturing apparatus, the surgical needle having a body portion, a relatively blunt tissue penetrating portion on at least one end of the body portion having a radius of approximately 0.005 to 0.015 inches, and a length of suture affixed to the body portion;

b) inserting the endoscopic suturing apparatus into a body cavity through a tubular cannula;

c) penetrating a first tissue section with the surgical needle;

d) moving the relatively blunt tissue penetrating portion along the surface of bony structure without causing permanent deformation of the body portion of the surgical needle;

e) penetrating a second tissue section with the surgical needle; and f) drawing the surgical needle through the first and second tissue sections to draw the length of suture through the first and second tissue sections.

* * * * *